(12) United States Patent
Lichy et al.

(10) Patent No.: US 11,857,145 B2
(45) Date of Patent: Jan. 2, 2024

(54) METHOD FOR PROVIDING IMAGE DATA OF A HOLLOW ORGAN

(71) Applicant: Siemens Healthcare GmbH, Erlangen (DE)

(72) Inventors: Matthias Lichy, Nuremberg (DE); Bernhard Schmidt, Fuerth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 753 days.

(21) Appl. No.: 16/819,347

(22) Filed: Mar. 16, 2020

(65) Prior Publication Data
US 2020/0305816 A1 Oct. 1, 2020

(30) Foreign Application Priority Data

Mar. 29, 2019 (EP) .................................... 19166066

(51) Int. Cl.
  *A61B 6/00* (2006.01)
  *A61B 6/03* (2006.01)
  *A61M 5/00* (2006.01)
(52) U.S. Cl.
  CPC .............. *A61B 6/481* (2013.01); *A61B 6/032* (2013.01); *A61B 6/4241* (2013.01); *A61B 6/469* (2013.01);
  (Continued)
(58) Field of Classification Search
  CPC ..... G06T 7/10–13; G06T 7/194; G06V 10/44; G06V 10/26; G06V 30/148
  See application file for complete search history.

(56) References Cited

U.S. PATENT DOCUMENTS 4,324,187 A 4/1982 Sambo
4,662,379 A 5/1987 Macovski
(Continued)

FOREIGN PATENT DOCUMENTS

DE 4410970 C1 7/1995
DE 4405505 A1 8/1995
(Continued)

OTHER PUBLICATIONS

Muenzel, D., et al., "Spectral Photon-counting CT: Initial Experience with Dual-Contrast Agent K-Edge Colonography", Radiology: vol. 283: No. Jun. 3, 2017. pp. 723-728. (Year: 2017).*
(Continued)

*Primary Examiner* — Pascal M Bui Pho
*Assistant Examiner* — Farouk A Bruce
(74) *Attorney, Agent, or Firm* — Harness, Dickey & Pierce, P.L.C.

(57) ABSTRACT

One embodiment relates to a method for providing image data of a hollow organ. The method includes applying a first contrast agent to a lumen of the hollow organ, to obtain a contrast agent filling of the lumen; applying a second contrast agent to a blood vessel system, the blood vessel system supplying a wall of the hollow organ, the second contrast agent having a different absorption spectrum than the first contrast agent; generating spectrally resolved computed tomography data of an examination area, the examination area including the hollow organ; calculating first image data indicative of a presence of the first contrast agent and second image data indicative of a presence of the second contrast agent by applying a material separation algorithm onto the spectrally resolved computed tomography data; and providing the image data of the hollow organ including the first image data and the second image data.

19 Claims, 4 Drawing Sheets

(52) U.S. Cl.
CPC .............. *A61B 6/50* (2013.01); *A61B 6/5205* (2013.01); *A61M 5/007* (2013.01)

(56) References Cited

U.S. PATENT DOCUMENTS

| | | | |
|---|---|---|---|
| 5,574,763 | A | 11/1996 | Dehner |
| 5,611,342 | A | 3/1997 | Widder |
| 6,650,724 | B2 | 11/2003 | Strobel |
| 6,950,493 | B2 | 9/2005 | Besson |
| 7,218,702 | B2 | 5/2007 | Mistretta et al. |
| 8,356,557 | B2 | 1/2013 | Schneider |
| 8,594,274 | B2 | 11/2013 | Hoernig et al. |
| 2004/0114706 | A1 | 6/2004 | Ikeda et al. |
| 2005/0180921 | A1* | 8/2005 | Taylor ................ A61K 49/0452 424/9.45 |
| 2006/0067473 | A1 | 3/2006 | Eberhard et al. |
| 2006/0109953 | A1* | 5/2006 | Walter .................. A61B 6/482 378/5 |
| 2008/0009702 | A1* | 1/2008 | Liu .................... A61B 5/02007 600/410 |
| 2008/0130824 | A1 | 6/2008 | Fujisawa |
| 2009/0022265 | A1 | 1/2009 | Takase et al. |
| 2009/0028289 | A1 | 1/2009 | Tsuyuki et al. |
| 2009/0028405 | A1 | 1/2009 | Degani et al. |
| 2009/0028409 | A1 | 1/2009 | Tsukagoshi et al. |
| 2009/0092225 | A1 | 4/2009 | Boese et al. |
| 2009/0129536 | A1 | 5/2009 | Ichihara et al. |
| 2009/0304253 | A1 | 12/2009 | Puong et al. |
| 2010/0091943 | A1 | 4/2010 | Kang et al. |
| 2011/0013815 | A1 | 1/2011 | Guendel |
| 2013/0163719 | A1 | 6/2013 | Tsujii |
| 2014/0072096 | A1 | 3/2014 | Hoernig |
| 2015/0245819 | A1* | 9/2015 | Yoshiara ............. A61B 8/0866 600/431 |
| 2016/0007943 | A1 | 1/2016 | Hoernig |
| 2016/0022233 | A1 | 1/2016 | Fieselmann et al. |

FOREIGN PATENT DOCUMENTS

| | | |
|---|---|---|
| DE | 10122875 C1 | 2/2003 |
| DE | 102007050438 A1 | 4/2009 |
| DE | 102009033452 A1 | 1/2011 |
| DE | 102010041920 A1 | 4/2012 |
| DE | 102012215997 A1 | 3/2014 |
| DE | 102014213464 A1 | 1/2016 |
| DE | 102014214772 A1 | 1/2016 |
| RU | 2376181 C2 | 12/2009 |
| WO | WO-2010/113045 A2 | 10/2010 |
| WO | WO 2017223343 A1 | 12/2017 |

OTHER PUBLICATIONS

Soesbe Todd C et al: "Separat inq High-Z Oral Contrast From Intravascular Iodine Contrast in an Animal Model Using Dual-Layer Spectral CT", Academic Radiology; Elsevier; Amsterdam; NL; vol. 26; No. 9; pp. 1237-1244; XP085758656; ISSN: 1076-6332; DOI: 10.1016/J.ACRA.2018.09.012.

Ruhr-Universität-Bochum, "Untersuchungen des Magengarmtrakts", http://www.ruhr-uni-bochum.de/radio-nuk-kkh/Institut/dl/DL.html (source of images).

Extended European Search Report dated Oct. 8, 2019.

R Karunamuni, et al., "Search for novel contrast materials in dual-energy x-ray breast imaging using theoretical modeling of contrast-to-noise-ratio," 2014, pp. 4311-4324, IP Science.

Marius Staring, et al., "Pulmonary Vessel Segmentation using Vessel Enhancement Filters," pp. 1-8.

Alejandro F. Frangi, et al., "Multiscale vessel enhancement filtering," 1998, pp. 130-137, vol. 1496, Springer Verlag, Berlin, Germany.

* cited by examiner

METHOD FOR PROVIDING IMAGE DATA OF A HOLLOW ORGAN

PRIORITY STATEMENT

The present application hereby claims priority under 35 U.S.C. § 119 to European patent application number EP 19166066.1 filed Mar. 29, 2019, the entire contents of which are hereby incorporated herein by reference.

FIELD

At least one embodiment of the invention generally relates to a method for providing image data of a hollow organ.

BACKGROUND

One of the tasks when reading computed tomography (CT) images is the assessment of vitality and integrity of organs and consequently tissue. In the case of CT scans with intravenous administered contrast agent, the presence of contrast media (CM) uptake in a region of interest regarding an anatomical region can be taken as an indicator for vitality, in particular in form of a surrogate of perfusion, of that anatomical region.

In homogeneous organs such as the liver or brain, iodine maps showing the presence of contrast media are helpful, giving clear guidance and supporting the reader for making diagnosis. Also, structural changes can be accessed and taken into consideration for diagnosis, e.g. high iodine uptake in a dedicated phase of liver perfusion can be indicative for certain types of malignancies like hepatocellular carcinoma. In case of inhomogeneous organs, reading from contrast media (CM) enhanced scans including iodine maps is more challenging because not only perfusion can be variable but also the structure of tissue is not homogenous and consequently variations of anatomy can be misinterpreted, and pathologies are easier to be missed.

For example in the case of the digestive system, where in addition to intra-venous administered agent also oral contrast agent is administered and anatomical structures are very variable, reading of CT images is even more challenging and takes lots of time and effort. The oral agent visualizes the lumen of small intestine and colon and stretches also the wall to reveal better the local anatomy. The intravenous agent visualizes the respective walls. With regard to the intravenous agent, enhancement indicates vitality, abnormal behavior indicates pathologies, e.g. cancer, and absence indicates ischemia and finally necrosis.

Several agents are used for x-ray-based examinations to visualize the lumen of the digestive system. Depending on the clinical questions, they are applied orally or injected directly to the area of interest via a catheter or drainage. This includes also rectal fillings in case of colon or rectal pathologies. In CT, also water and air (for virtual colonoscopy) are applied. However, often these oral agents contain dense materials, for example iodine or barium, to visualize the lumen and also to visualize better stenosis and abnormalities in the passage of this agent when taken orally.

In CT, barium containing agents are not used anymore widely because of the severe side effects when this material contaminates the peritoneum, e.g. in case of perforated appendicitis. However, contrast agents for the lumen which contain high attenuating materials like iodine are also supporting the detection of small perforations which are hard to visualize when applying water due to a lack of differentiation between edema/ascites and oral given water which leaks into the peritoneum as consequence of a e.g. bowel perforation.

In conventional x-ray-based exams (e.g. fluoroscopy), often a combination of dynamic imaging and so-called double contrast techniques are used to visualize textural changes. Therefore, a large tumor of the colon will often result in irregular stenosis of the lumen and irregular loss of wall structure whereas an inflammatory process will result in a more regular stenosis and a regular loss of texture. These patterns are often typical image patterns for certain diseases like Morbus Crohn or Colitis ulcerosa.

In the case of virtual colonoscopy with CT, air is used to extend the colon and, based on volume rendering techniques (VRTs), a "fly-through" visualization of the colon is simulated to generate a similar view as achieved with conventional colonoscopy. However, visualization of pathologies is often limited because this approach requires a perfect unfolding of the colonic wall without any contamination, e.g. by stool, to be able to display also smaller pathologies like polyps.

Visualization of the wall is simply based on very high attenuation difference between soft tissue and air. The attenuation may be measured in Hounsfield units (HU). Very dense stool and content can in rare cases also achieve very high HU values which can be similar to the attenuation resulting from intravenous CM application.

If high attenuating materials like iodine are used as oral contrast agents, the brightness of the CM enhanced lumen can mask the stretched wall and the enhancement under certain circumstances. Also the application of iodine maps is not helpful in such a case because there is no differentiation between the wall enhancement and the density of the intraluminal iodine. Based on conventional CT images, no further visualization of the digestive system can be achieved because current algorithms cannot differentiate between the HU changes of oral and intravenous CM, which results in comparable pictures gained by fluoroscopy. In addition, CM enhancement of parenchymal organs will overlay conventional projection approaches and result in non-diagnostic images.

Masking of pathologies by oral and intravenous CM application can be compensated by performing multiple scans to gain also dynamic information which can be used for further diagnosis. This often results in a time consuming and tiring reading process.

SUMMARY

The inventors have discovered that an underlying technical problem is to facilitate an improved assessment of a different parts of a hollow organ. This problem is improved upon or even solved by at least one embodiment of the present application. The claims are related to embodiments of the invention.

In one embodiment, the invention relates to a method for providing image data of a hollow organ, comprising applying a first contrast agent to a lumen of the hollow organ, to obtain a contrast agent filling of the lumen and/or thereby obtaining a contrast agent filling of the lumen, applying a second contrast agent to a blood vessel system, the blood vessel system supplying a wall of the hollow organ, the second contrast agent having a different absorption spectrum than the first contrast agent, generating spectrally resolved computed tomography data of an examination area, in particular an examination area of a patient, in particular, a human patient, the examination area comprising the hollow organ, calculating first image data indicative of a presence of the first contrast agent and second image data indicative of a presence of the second contrast agent by applying a material separation algorithm onto the spectrally resolved computed tomography data, and providing the image data of the hollow organ comprising the first image data and the second image data.

Reference is made to the fact that the described methods and the described units are merely preferred example embodiments of the invention and that the invention can be varied by a person skilled in the art, without departing from the scope of the invention as it is specified by the claims.

BRIEF DESCRIPTION OF THE DRAWINGS

The invention will be illustrated below with reference to the accompanying figures using example embodiments. The illustration in the figures is schematic and highly simplified and not necessarily to scale.

DETAILED DESCRIPTION OF THE EXAMPLE EMBODIMENTS

Figure 1:
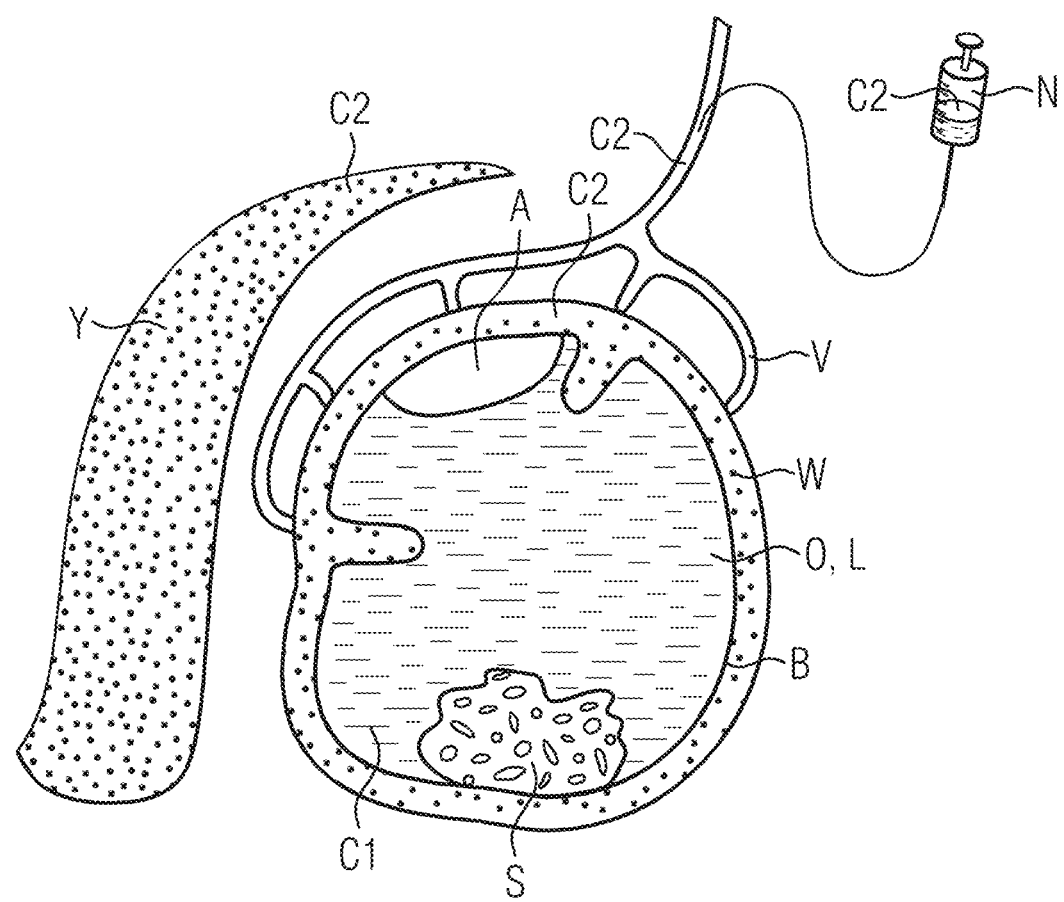
FIG. 1 shows a hollow organ with a first contrast agent and a second contrast agent applied to the hollow organ.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In one embodiment, the invention relates to a method for providing image data of a hollow organ, comprising
  applying a first contrast agent to a lumen of the hollow organ, to obtain a contrast agent filling of the lumen and/or thereby obtaining a contrast agent filling of the lumen,
  applying a second contrast agent to a blood vessel system, the blood vessel system supplying a wall of the hollow organ, the second contrast agent having a different absorption spectrum than the first contrast agent,
  generating spectrally resolved computed tomography data of an examination area, in particular an examination area of a patient, in particular, a human patient, the examination area comprising the hollow organ,
  calculating first image data indicative of a presence of the first contrast agent and second image data indicative of a presence of the second contrast agent by applying a material separation algorithm onto the spectrally resolved computed tomography data, and
  providing the image data of the hollow organ comprising the first image data and the second image data.

The spectrally resolved computed tomography data may be generated, for example, by scanning the examination area using a spectral CT technique. In particular, the spectrally resolved computed tomography data are acquired while the first contrast agent and the second contrast agent both are present in the examination area comprising the hollow anatomical structure. For example, if the first contrast agent is applied orally and the second contrast agent is applied intravenously, the first contrast agent may be applied significantly earlier than the second contrast agent. The contrast agent filling of the lumen may be a liquid contrast agent filling and/or may consist substantially of the first contrast agent.

The spectrally resolved computed tomography data may be, for example, photon counting computed tomography data, dual source computed tomography data or split filter computed tomography data. In particular, spectrally resolved computed tomography data may be generated that allow extraction of at least two energy levels, preferable three energy levels.

The material separation algorithm may be, for example, a k-edge imaging algorithm. The material separation algorithm may be configured to separate both contrast agents from each other and quantify each of the contrast agents. For example, the material separation algorithm may be configured to calculate a two or three material decomposition based on the spectrally resolved computed tomography data.

A region of interest in the image data may be determined, for example, based on a user input in a graphical user interface that displays the image data. The region of interest in the image data may be classified, in particular automatically classified, in respect of the presence of the first contrast agent and the presence of the second contrast agent.

The region of interest may be classified, for example, as either comprising both the first contrast agent and the second contrast agent or missing at least one of the first contrast agent and the second contrast agent. Only when both agents are present in a region of interest (ROI), that ROI is close to the wall (according to the presence of the first contrast agent) and perfusion is happening (according to the presence of the second contrast agent). If first contrast agent is not in the ROI, the assessed ROI is not close to the wall of the lumen at all. This allows removal of intrinsically distracting, non-relevant structures.

A representation of a border of the contrast agent filling of the lumen may be generated based on the first image data. The representation of the border of the contrast agent filling of the lumen can be generated, for example, by applying a segmentation algorithm onto the first image data.

A representation of the wall of the hollow organ may be generated based on the representation of the border of the contrast agent filling of the lumen and the second image data.

A position of the wall of the hollow anatomical structure can be determined, for example, based on the representation of the border of the contrast agent filling of the lumen. For example, pixels of the second image data that are located adjacent to and/or in very close surroundings of the border of the contrast agent filling of the lumen and show presence of the second contrast agent, in particular, exceeding a predefined threshold value for the presence of the second contrast agent, may be assigned to the representation of the wall of the hollow organ.

The presence of the second contrast agent at the position of the wall of the hollow anatomical structure is indicative, in particular, of a perfusion of the wall, and therefore of a vitality of the wall. Missing the second contrast agent at the position of a given region of the wall may indicate potential presence of necrosis and/or ischemia in that region of the wall.

In another embodiment, a representation of a plurality of anatomical structures comprising the second contrast agent is generated based on the second image data. A region of the representation of the plurality of anatomical structures may be determined, the region being adjacent to the representation of the border of the contrast agent filling of the lumen. The representation of the wall of the hollow organ may be generated based on the region of the representation of the plurality of anatomical structures that is adjacent to the representation of the border of the contrast agent filling of the lumen. For example, at least one part of the representation of the plurality of anatomical structures can be selected that is adjacent to the representation of the border of the contrast agent filling of the lumen, thereby obtaining the representation of the wall of the hollow organ.

For example, a region of the representation of the plurality of anatomical structures can be considered adjacent to the representation of the border of the contrast agent filling of the lumen, if for each pixel of that region the distance between that pixel and the representation of the border of the contrast agent filling of the lumen is below a predefined threshold value for the distance.

The lumen of the hollow organ may comprise at least one portion external to the contrast agent filling of the lumen and adjacent to the wall of the hollow structure. A representation of the at least one portion of the lumen may be generated based on the representation of the border of the contrast agent filling of the lumen and the representation of the wall of the hollow organ.

The image data may comprise at least one of the representation of the border of the contrast agent filling of the lumen, the representation of the wall of the hollow organ, and the representation of the at least one portion of the lumen that is external to the contrast agent filling of the lumen and adjacent to the wall of the hollow structure. The image data can be provided, for example, by transmitting a signal that carries the image data and/or by writing the image data into a computer-readable medium and/or by displaying the image data on a display.

Each of the representations mentioned herein may be visualized, for example, using two-dimensional and/or three-dimensional methods, in particular in form of a layer and/or a surface. In particular, a 2D and/or 3D image of the wall of the hollow organ may be generated, showing only the areas of double contrast, i. e. presence of both agents in close surrounding, being an indicator for vital tissue of the wall of the hollow organ. Holes and missing structures in such an image indicate necrosis and/or ischemia. This allows a faster and more comfortable reading of the image data.

The hollow organ may be an organ of the digestive system, for example, a bowel. The hollow organ may be, for example, a colon or a small intestine. The at least one portion of the lumen may comprise, in particular may consist of, a solid material, for example, dense stool, and/or a gas, for example, air. The first contrast agent may be applied, for example, orally or in form of a rectal filling. The second contrast agent may be applied intravenously.

In another embodiment, the first contrast agent is based on a first material with a first k-edge and the second contrast agent is based on a second material with a second k-edge. The second contrast agent has a different absorption spectrum than the first contrast agent, for example, if the distance between the first k-edge and the second k-edge is non-zero, in particular, at least 1 Kiloelectronvolt, for example, at least 10 Kiloelectronvolts, and/or if the absorption spectrum of the second agent has a different shape than the absorption spectrum of the first agent. The distance between the first k-edge and the second k-edge may be at least 10 Kiloelectronvolts, for example at least 15 Kiloelectronvolts, in particular, at least 20 Kiloelectronvolts.

In another embodiment, the first contrast agent is based on tungsten, holmium or gadolinium and/or the second contrast agent is based on iodine or barium. In another embodiment, the second contrast agent is based on tungsten, holmium or gadolinium and/or the first contrast agent is based on iodine or barium.

For example, the first contrast agent may be gadolinium-based, and the second contrast agent may be iodine-based. In another embodiment, the first contrast agent is based on iron or manganese and/or the second contrast agent is based on iodine or barium.

Wherever not already described explicitly, individual embodiments, or their individual aspects and features, can be combined or exchanged with one another without limiting or widening the scope of the described invention, whenever such a combination or exchange is meaningful and in the sense of this invention. Advantages which are described with respect to one embodiment of the present invention are, wherever applicable, also advantageous of other embodiments of the present invention.

In the context of the present invention, the expression "based on" can in particular be understood as meaning "using, inter alia". In particular, wording according to which a first feature is calculated (or generated, determined etc.) based on a second feature does not preclude the possibility of the first feature being calculated (or generated, determined etc.) based on a third feature.

Reference is made to the fact that the described methods and the described units are merely preferred example embodiments of the invention and that the invention can be varied by a person skilled in the art, without departing from the scope of the invention as it is specified by the claims.

FIG. 1 shows a hollow organ O with a first contrast agent C1 and a second contrast agent C2 applied to the hollow organ O. The first contrast agent C1 is applied to the lumen L of the hollow organ O. The first contrast agent C1 accumulates in the lumen L of the hollow organ O and forms a contrast agent filling of the lumen L.

The second contrast agent C2 is applied to a blood vessel system V using an injector N. The blood vessel system V supplies the wall W of the hollow organ O and a parenchymal organ Y. The second contrast agent C2 accumulates in the blood vessel system V, the wall W of the hollow organ O and the parenchymal organ Y. The wall W of the hollow organ O is encompassing the lumen L of the hollow organ O. The parenchymal organ Y is separated from the hollow organ O, for example by an interlayer of fat.

The hollow organ O shown in FIG. 1 is a bowel. The lumen L of the hollow organ O comprises two portions A and S, each being external to the contrast agent filling of the lumen L and adjacent to the wall W of the hollow organ O. Portion A consists of air. Portion S consists of stool. The parenchymal organ Y shown in FIG. 1 is spleen.

Figure 2:
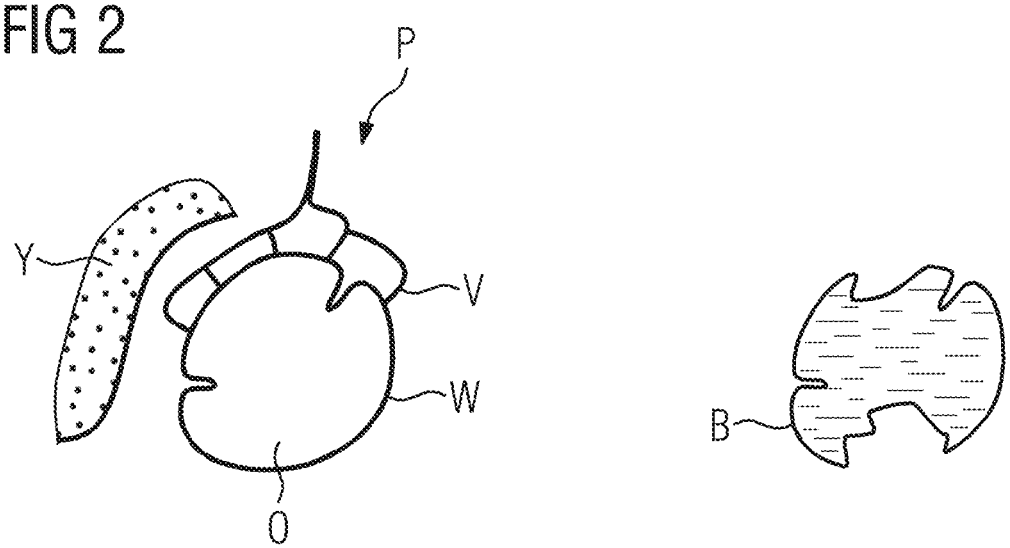
FIG. 2 shows a plurality of anatomical structures and a border of a contrast agent filling of a lumen.

FIG. 2 shows a plurality P of anatomical structures comprising the second contrast agent C2 and a border B of a contrast agent filling of the lumen L. The plurality P of anatomical structures comprises the blood vessel system V, the wall W of the hollow organ O and the parenchymal organ Y. Significant amounts of the second contrast agent C2 are present in each of these anatomical structures. In the second image data, the plurality P of anatomical structures is enhanced by the second contrast agent C2.

The border B of the contrast agent filling of the lumen L follows the wall W of the hollow organ O with exception of those parts, where the border B of the contrast agent filling of the lumen L is separated from the wall W of the hollow organ O by portion A or portion S.

Figure 3:
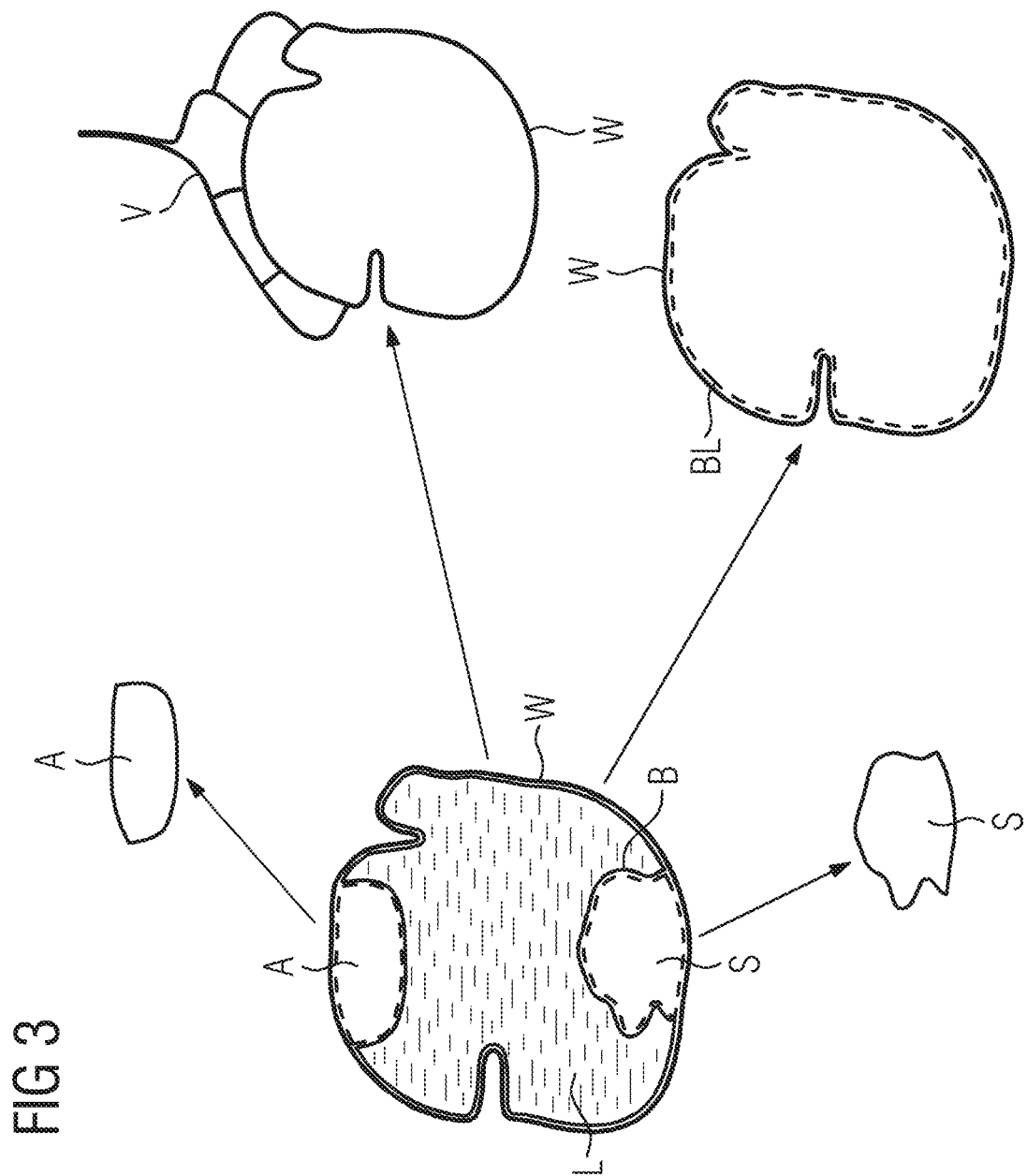
FIG. 3 shows representations of different parts of the hollow organ.

FIG. 3 shows representations of different parts of the hollow organ O, in particular the representation of the wall W of the hollow organ O, the representation of the border B of the contrast agent filling of the lumen L, a representation of the portion A and a representation of the portion S. Furthermore, a representation of the border BL of the lumen L is shown. The representation of the border BL of the lumen L can be generated based on the representation of the border B of the contrast agent filling of the lumen L and the representation of the wall W of the hollow organ O. In particular, based on the representation of the wall W of the hollow organ O a course of the border BL of the lumen L can be estimated for those parts, where the border B of the contrast agent filling of the lumen L is separated from the wall W of the hollow organ O by portion A or portion S.

Figure 4:
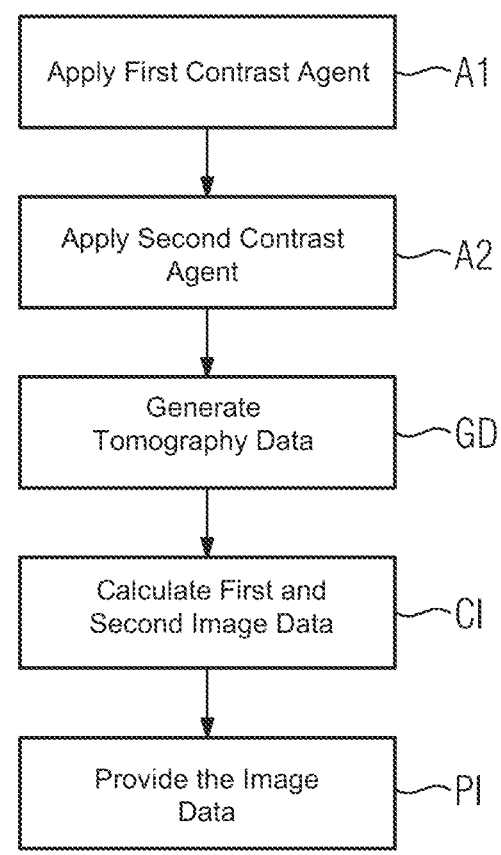
FIG. 4 shows a diagram illustrating a method for providing image data of a hollow organ.

FIG. 4 shows a diagram illustrating a method for providing image data of a hollow organ O, comprising
  applying A1 a first contrast agent C1 to a lumen L of the hollow organ O, thereby obtaining a contrast agent filling of the lumen L,
  applying A2 a second contrast agent C2 to a blood vessel system V supplying a wall W of the hollow organ O, the second contrast agent C2 having a different absorption spectrum than the first contrast agent C1,
  generating GD spectrally resolved computed tomography data of an examination area of a patient comprising the hollow organ O,
  calculating CI first image data indicative of a presence of the first contrast agent C1 and second image data indicative of a presence of the second contrast agent C2 by applying a material separation algorithm onto the spectrally resolved computed tomography data, and
  providing PI the image data of the hollow organ O comprising the first image data and the second image data.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for providing image data of a hollow organ of a digestive system, comprising:
  applying a first contrast agent to a lumen of the hollow organ to obtain a contrast agent filling of the lumen, the first contrast agent having a first absorption spectrum;
  applying a second contrast agent to a blood vessel system supplying a wall surrounding the lumen of the hollow organ, the second contrast agent providing substantially complete perfusion of the wall, and the second contrast agent having a second absorption spectrum different from the first absorption spectrum;

generating spectrally resolved computed tomography data of an examination area including the hollow organ;

calculating first image data and second image data by applying a material separation algorithm onto the spectrally resolved computed tomography data, the first image data indicative of a presence of the first contrast agent, and the second image data indicative of a presence of the second contrast agent;

generating a representation of the wall based on the first image data and the second image data, the generating the representation of the wall including assigning a pixel of the second image data to the representation of the wall based on a distance of the pixel from a representation of a border of the first contrast agent filling of the lumen; and providing the representation of the wall.

2. The method of claim 1, wherein the spectrally resolved computed tomography data are photon counting computed tomography data.

3. The method of claim 2, wherein the material separation algorithm is a k-edge imaging algorithm.

4. The method of claim 2, the method further comprising:
determining a region of interest in the image data; and
classifying the region of interest based on the presence of the first contrast agent and the presence of the second contrast agent.

5. The method of claim 2, wherein the generating the representation of the wall includes generating the representation of the border of the first contrast agent filling of the lumen based on the first image data.

6. The method of claim 1, wherein the material separation algorithm is a k-edge imaging algorithm.

7. The method of claim 6, the method further comprising:
determining a region of interest in the image data; and
classifying the region of interest based on the presence of the first contrast agent and the presence of the second contrast agent.

8. The method of claim 1, the method further comprising:
determining a region of interest in the image data; and
classifying the region of interest based on the presence of the first contrast agent and the presence of the second contrast agent.

9. The method of claim 1, wherein the generating the representation of the wall includes,
generating the representation of the border of the first contrast agent filling of the lumen based on the first image data.

10. The method of claim 9, wherein the generating the representation of the wall includes,
generating a representation of a plurality of anatomical structures based on the second image data,
determining a region of the representation of the plurality of anatomical structures, the region being adjacent to the representation of the border of the first contrast agent filling of the lumen, and
generating the representation of the wall based on the region of the representation of the plurality of anatomical structures.

11. The method of claim 10, wherein
the lumen of the hollow organ includes at least one portion external to the first contrast agent filling of the lumen and adjacent to the wall, and
the generating the representation of the wall includes generating a representation of the at least one portion of the lumen based on the representation of the border of the first contrast agent filling of the lumen.

12. The method of claim 9, wherein
the lumen of the hollow organ includes at least one portion external to the first contrast agent filling of the lumen and adjacent to the wall of the hollow organ, and
the generating the representation of the wall includes generating a representation of the at least one portion of the lumen based on the representation of the border of the first contrast agent filling of the lumen.

13. The method of claim 12, wherein the at least one portion of the lumen includes at least one of a solid material or a gas.

14. The method of claim 1, wherein the hollow organ is a colon or a small intestine.

15. The method of claim 1, wherein the applying the first contrast agent includes applying the first contrast agent orally.

16. The method of claim 1, wherein the applying the second contrast agent includes applying the second contrast agent intravenously.

17. The method of claim 1, wherein
the first contrast agent is based on a first material with a first k-edge,
the second contrast agent is based on a second material with a second k-edge, and
a distance between the first k-edge and the second k-edge is at least 10 Kiloelectronvolts.

18. The method of claim 1, wherein at least one of
the first contrast agent is based on a first element selected from the group comprising tungsten, holmium and gadolinium, or
the second contrast agent is based on a second element selected from the group comprising iodine and barium.

19. The method of claim 1, wherein the pixel is assigned to the representation of the wall based on a value of the pixel exceeding a threshold value, the value indicating an amount of the second contrast agent present.

* * * * *